United States Patent
Sugiyama et al.

(10) Patent No.: US 10,463,316 B2
(45) Date of Patent: Nov. 5, 2019

(54) MEDICAL INFORMATION PROCESSING SYSTEM

(71) Applicant: Toshiba Medical Systems Corporation, Otawara-shi (JP)

(72) Inventors: Atsuko Sugiyama, Nasushiobara (JP); Mariko Shibata, Nasushiobara (JP); Yoshimasa Kobayashi, Nasushiobara (JP); Kei Mori, Shioya (JP); Koichi Terai, Shioya (JP); Toshie Maruyama, Yaita (JP)

(73) Assignee: Canon Medical Systems Corporation, Otawara-shi (JP)

( * ) Notice: Subject to any disclaimer, the term of this patent is extended or adjusted under 35 U.S.C. 154(b) by 242 days.

(21) Appl. No.: 15/700,358

(22) Filed: Sep. 11, 2017

(65) Prior Publication Data
US 2018/0070892 A1    Mar. 15, 2018

(30) Foreign Application Priority Data

Sep. 12, 2016  (JP) ................. 2016-178064
Sep. 7, 2017   (JP) ................. 2017-172199

(51) Int. Cl.
    *A61B 6/02*       (2006.01)
    *A61B 6/00*       (2006.01)
    (Continued)

(52) U.S. Cl.
    CPC .............. *A61B 6/025* (2013.01); *A61B 5/055* (2013.01); *A61B 6/0414* (2013.01); *A61B 6/466* (2013.01); *A61B 6/469* (2013.01); *A61B 6/502* (2013.01); *A61B 6/5217* (2013.01); *A61B 6/5247* (2013.01); *A61B 6/54* (2013.01); *A61B 6/563* (2013.01); *A61B 8/468* (2013.01)

(58) Field of Classification Search
    CPC ....... A61B 6/025; A61B 6/469; A61B 6/5247; A61B 6/563; A61B 8/468; A61B 6/0414; A61B 6/5217; A61B 6/502; A61B 6/54; A61B 6/466; A61B 5/055
    See application file for complete search history.

(56) References Cited

U.S. PATENT DOCUMENTS

2012/0262460 A1    10/2012  Endo et al.
2015/0070385 A1*    3/2015  Ishizu .................... A61B 6/461
                                                        345/632

(Continued)

FOREIGN PATENT DOCUMENTS

JP    2012-217770    11/2012
JP    2015-027450     2/2015

*Primary Examiner* — Michael C Bryant
(74) *Attorney, Agent, or Firm* — Oblon, McClelland, Maier & Neustadt, L.L.P.

(57) ABSTRACT

A medical information processing system includes setting circuitry, generating circuitry and output control circuitry. The setting circuitry is configured to set a region of interest in a three-dimensional image that is generated by emitting X-rays to a breast of a subject and imaging the breast from different directions. The generating circuitry is configured to generate reference information in which positional information about the region of interest is associated with a schematic diagram of the breast. The output control circuitry is configured to cause output circuitry to output the reference information.

12 Claims, 14 Drawing Sheets

(51) Int. Cl.
*A61B 5/055* (2006.01)
*A61B 6/04* (2006.01)
*A61B 8/00* (2006.01)

(56) References Cited

U.S. PATENT DOCUMENTS

2016/0110875 A1* 4/2016 Sugiyama ............ A61B 8/0825
                                                        382/131
2017/0128037 A1* 5/2017 Mori .................... A61B 8/0825
2018/0220994 A1* 8/2018 Sugiyama ............ A61B 8/0825

* cited by examiner

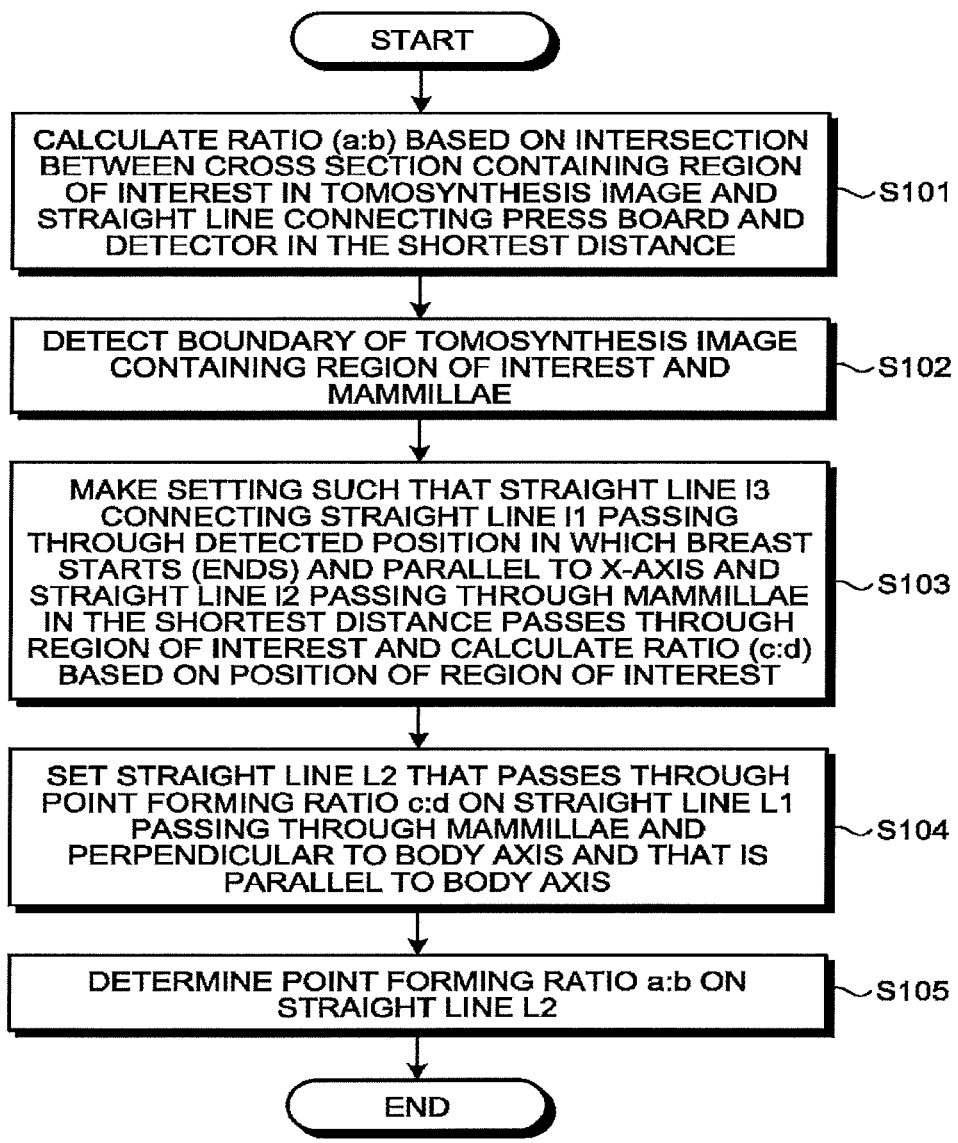

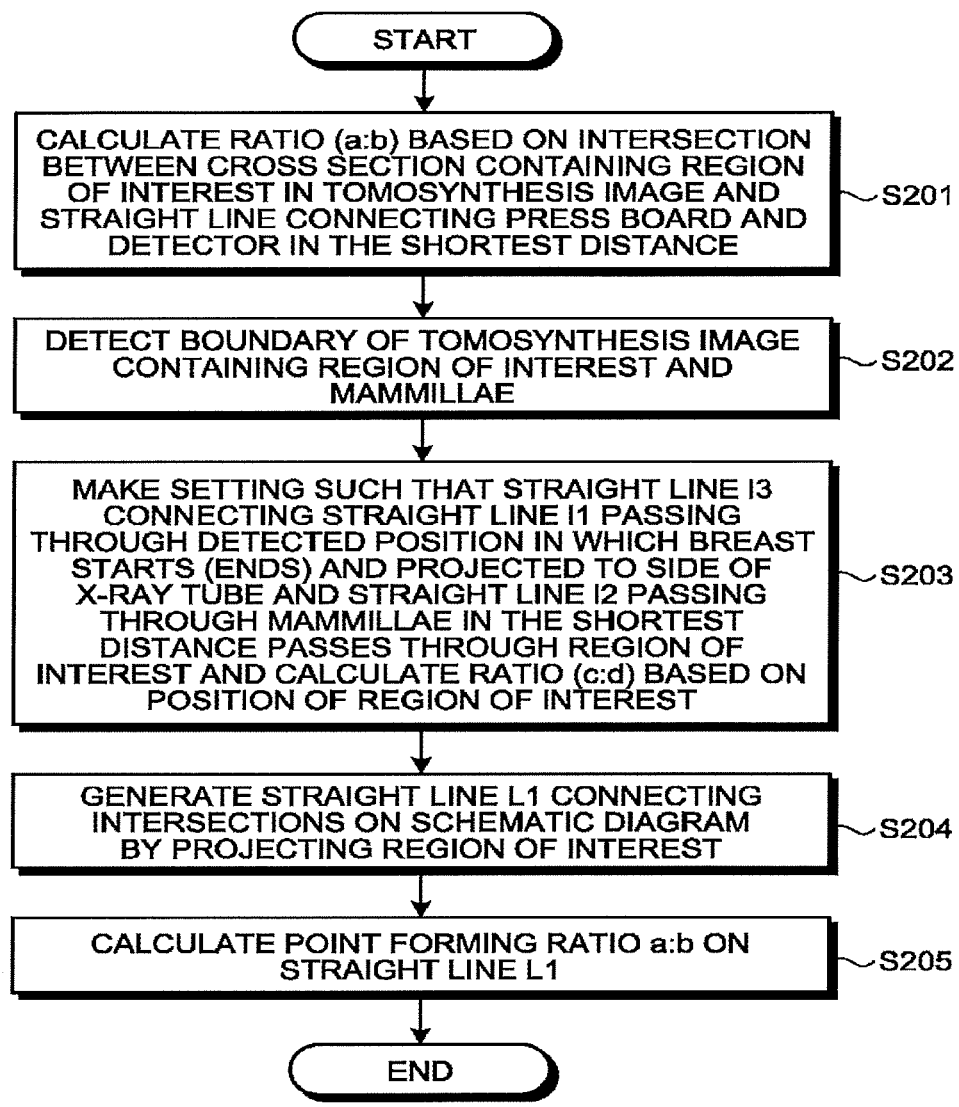

MEDICAL INFORMATION PROCESSING SYSTEM

CROSS-REFERENCE TO RELATED APPLICATIONS

This application is based upon and the benefit of priority from Japanese Patent Application No. 2016-178064, filed on Sep. 12, 2016; and Japanese Patent Application No. 2017-172199, filed on Sep. 7, 2017, entire contents of all of which are incorporated herein by reference.

FIELD

Embodiments described herein relate generally to a medical information processing system.

BACKGROUND

In breast cancer screening, a medical image diagnostic device, such as a mammography device, an ultrasound diagnostic device or a magnetic resonance device, captures breast images. In breast cancer screening, a diagnosis may be made not by performing radiologic interpretation on breast images captured by a single medical image diagnostic device but also by supplementarily performing radiologic interpretation in breast images captured by multiple medical image diagnostic devices. For example, radiologic interpretation using both mammographic images captured by a mammography device and ultrasound images of mammary glands captured by an ultrasound diagnostic device is performed.

In recent years, many mammography devices use Tomosynthesis imaging of generating a three-dimensional image by imaging a breast a subject being fixed while changing the angle at which an X-ray is emitted the breast of the subject. Mammographic images generated by Tomosynthesis imaging are referred to as Tomosynthesis images.

BRIEF DESCRIPTION OF THE DRAWINGS

FIG. 8 is a flowchart illustrating a process procedure performed by the image processing device according to the first embodiment;

FIG. 10 is a flowchart (2) illustrating a process procedure performed by the image processing device according to the first embodiment;

DETAILED DESCRIPTION

Embodiments of a medical information processing system will be described with reference to the accompanying drawings.

A medical information processing system according to one embodiment includes setting circuitry, generating circuitry and output control circuitry. The setting circuitry is configured to set a region of interest in a three-dimensional image that is generated by emitting X-rays to a breast of a subject and imaging the breast from different directions. The generating circuitry is configured to generate reference information in which positional information about the region of interest is associated with a schematic diagram of the breast. The output control circuitry is configured to cause output circuitry to output the reference information.

First Embodiment

Figure 1:
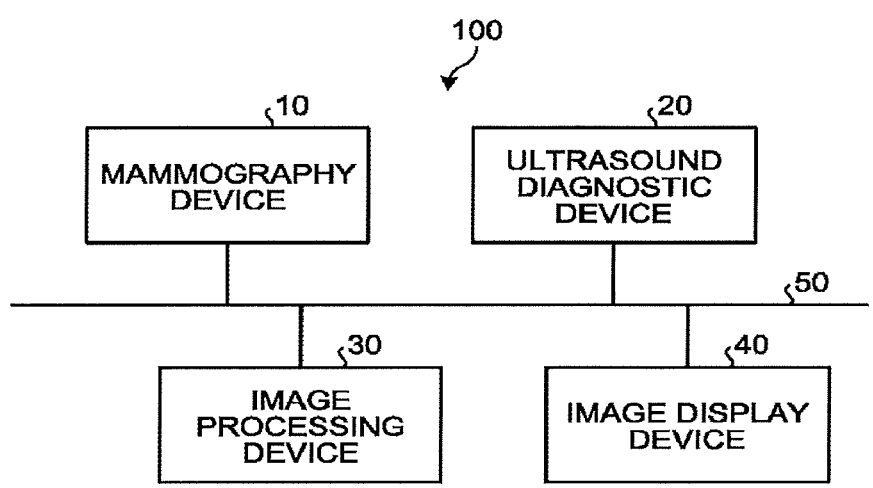
FIG. 1 is a diagram illustrating an exemplary configuration of a medical information processing system according to a first embodiment.

FIG. 1 is a diagram illustrating an exemplary configuration of a medical information processing system 100 according to a first embodiment. The medical information processing system 100 according to the first embodiment is set in a hospital where breast cancer screening is carried out and is used for a breast image diagnosis using both mammographic images and ultrasound images. For example, as illustrated in FIG. 1, the medical information processing system 100 according to the embodiment includes a mammography device 10, an ultrasound diagnostic device 20, an image processing device 30, and an image display device 40. The devices are connected to one another via a network 50 and transmit and receive images captured by the mammography devices 10 and the ultrasound diagnostic device 20 to one another. For example, when the medical information processing system 100 has a picture archiving and communication system (PACS) introduced thereto, each of the devices transmits and receive medical image data, etc., in a Digital Imaging and Communications in Medicine (DICOM) format obtained by adding additional information to medical image data. The additional information includes, for example, a patient identifier (ID) that identifies a patient, an examination ID that identifies an examination, a device ID that identifies each device and a series ID that identifies one set of imaging by each device.

The mammography device 10 emits X-rays to a breast of a subject and detects the X-rays having transmitted through the breast to generate a mammographic image.

Figure 2:
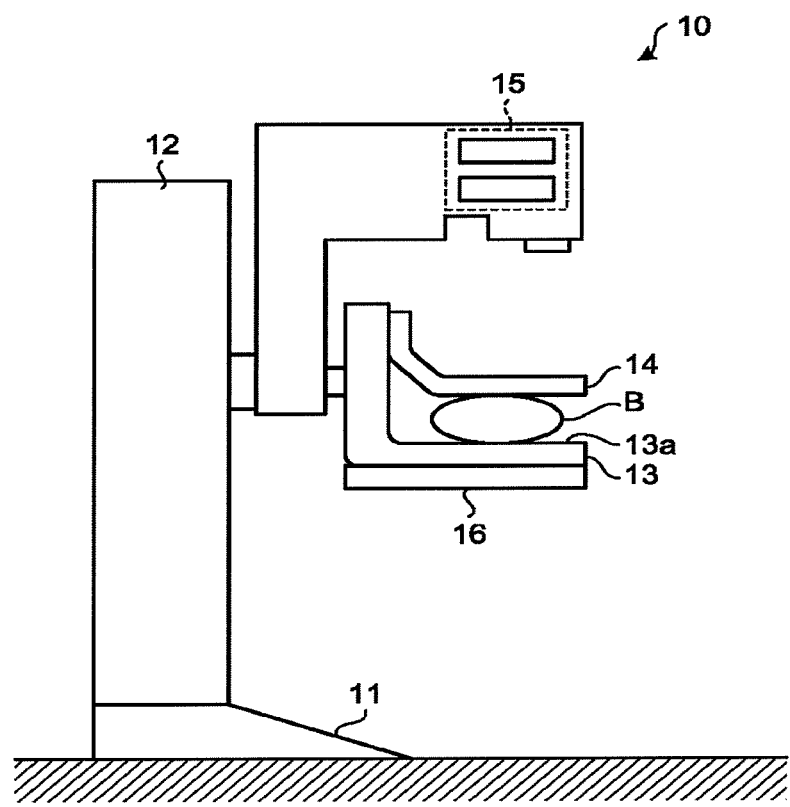
FIG. 2 is a diagram (1) illustrating an exemplary configuration of a mammography device according to the first embodiment.
Figure 3:
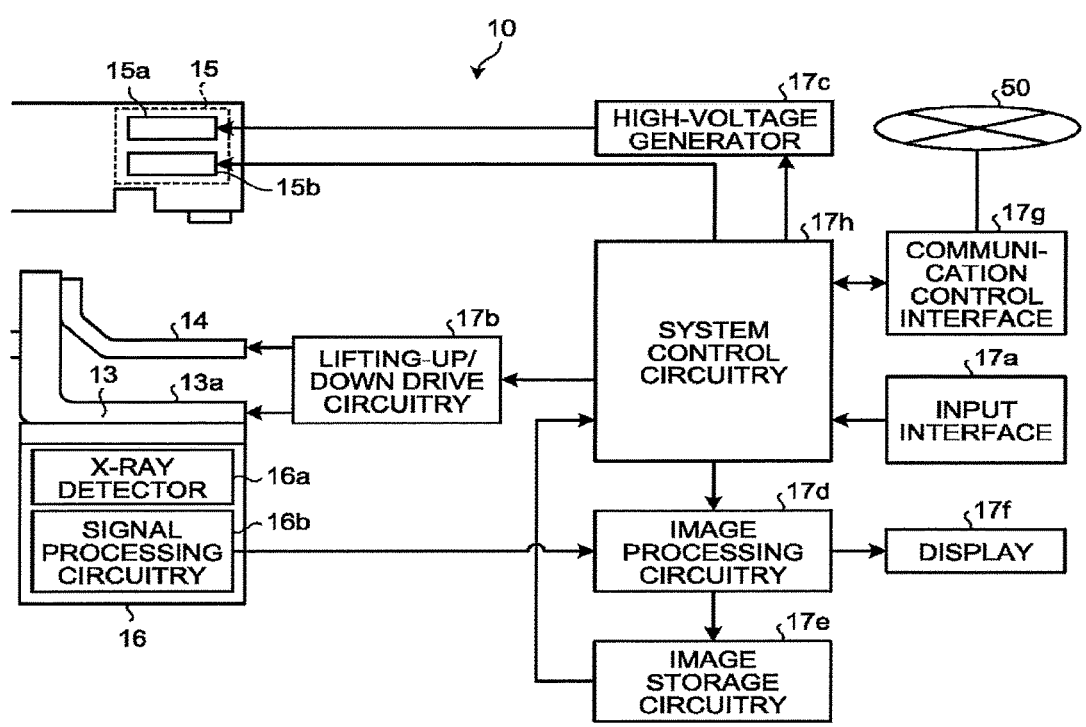
FIG. 3 is a diagram (2) illustrating an exemplary configuration of a mammography device according to the first embodiment.

FIGS. 2 and 3 are diagrams illustrating exemplary configurations of the mammography device 10 according to the first embodiment. For example, as illustrated in FIG. 2, the mammography device 10 includes a base 11 and a stand 12. The stand 12 is vertically arranged on the base 11 and supports an imaging table 13, a press board 14, an X-ray output device 15 and an X-ray detection device 16. The imaging table 13, the press board 14 and the X-ray detection device 16 are supported vertically movably.

The imaging table 13 is a table that supports a breast B of the subject and has a support surface 13a on which the breast B is put. The press board 14 is arranged above the imaging table 13. The press board 14 faces the imaging table 13 in parallel to the imaging table 13 and is provided movably in directions in which the press board 14 approaches and separates from the imaging table 13. When the press board 14 moves in the direction in which the press board 14 approaches the imaging table 13, the press board 14 presses the breast B supported on the imaging table 13. The breast B pressed by the press board 14 is pushed out to be thin and thus the overlap of mammary glands in the breast B reduces.

Furthermore, as illustrated in FIG. 3, the mammography device 10 includes an input interface 17a, lifting-up/down drive circuitry 17b, a high-voltage generator 17c, image processing circuitry 17d, image storage circuitry 17e, a display 17f, a communication control interface 17g, and system control circuitry 17h. The input interface 17a receives operations of inputting various commands from an operator. The lifting-up/down drive circuitry 17b is connected to the imaging table 13 and causes the imaging table 13 to lift up or down vertically. Furthermore, the lifting-up/down drive circuitry 17b is connected to the press board 14 and causes the press board 14 to lift up or down vertically (in the direction in which the press board 14 approaches or separates from the imaging table 13).

The X-ray output device 15 includes an X-ray tube 15a and an X-ray diaphragm 15b. The X-ray tube 15a generates X-rays. The X-ray diaphragm 15b is arranged between the X-ray tube 15a and the press board 14 and controls the area to which the X-rays generated by the X-ray tube 15a are emitted. The high-voltage generator 17c is connected to the X-ray tube 15a and supplies a high voltage for the X-ray tube 15a to generate X-rays.

The X-ray output device 15 is capable of Tomosynthesis imaging. In Tomosynthesis imaging, the positions of the imaging table 13 and the press board 14 are fixed and, while the angle of the X-ray tube 15a with respect to the breast is being changed, X-rays are output to a breast of a subject kept pressed.

The X-ray detection device 16 includes an X-ray detector 16a and signal processing circuitry 16b. The X-ray detector 16a detects the X-rays having transmitted the breast F and the imaging table 13 and converts the X-rays into electric signals (transmitted X-ray data). The signal processing circuitry 16b generates X-ray projection data from the electric signals that are converted by the X-ray detector 16a.

The image processing circuitry 17d is connected to the signal processing circuitry 16b and the image storage circuitry lie and generates a mammographic image on the basis of the X-ray projection data that is generated by the signal processing circuitry 16b. For example, the image processing circuitry 17d generates a mammographic image (MLO image) on the basis of X-ray projection data that is generated by fixing the positions of the imaging table 13 and the press board 14 in a mediolateral-oblique (MLO) direction and outputting X-rays without changing the angle of the X-ray tube 15a to the breast. Furthermore, the image processing circuitry 17d generates a mammographic image (CC image) on the basis of X-ray projection data that is generated by fixing the positions of the imaging table 13 and the press board 14 in a cranio-caudal direction and outputting X-rays without hanging the angle of the X-ray tube 15a to the breast.

The image processing circuitry 17d further generates a Tomosynthesis image that is a three-dimensional image on the basis of an image obtained by imaging the subject at various angles. In other words, a three-dimensional image is generated on the basis of the images obtained by the X-ray mammography device 10 through Tomosynthesis imaging. For example, the image processing circuitry 17d generates a Tomosynthesis image (a MLO Tomosynthesis image) on the basis of X-ray projection data that is generated by fixing the imaging table 13 and the press board 14 in the MLO direction and outputting X-rays without changing the angle of the X-ray tube 15a to the breast. Furthermore, the image processing circuitry 17d generates a Tomosynthesis image (CC Tomosynthesis image on the basis of X-ray projection data that is generated by fixing the imaging table 13 and the press board 14 in the CC direction and outputting X-rays while the angle of the X-ray tube 15a to the breast is being changed.

Specifically, the image processing circuitry 17d generates a Tomosynthesis image by performing given processing on the basis of multiple images corresponding respectively to the multiple angles to the subject. The given processing includes, for example, a shifting and adding method, a filtered back projection (FBP) method. In other words, through Tomosynthesis imagine, a three-dimensional image is generated by emitting X-rays from the X-ray tube 15a to the breast of the subject and imaging the breast from different directions. In the following descriptions, mammographic images cover MLO Tomosynthesis images and CC Tomosynthesis images in addition to MLO images and CC images. In order to be distinguished from Tomosynthesis images, MLO images and CC images will be referred to as two-dimensional mammographic images below. For example, an MLO image will be referred to as a two-dimensional MLO image and a CC image will be referred to as a two-dimensional CC iamge.

The image processing circuitry 17d saves the generated mammographic images in the image storage circuitry 17e. The image processing circuitry 17d is connected to the display 17f and displays the generated mammographic images on the display 17f. The image processing circuitry 17d is able to switch the type of mammographic images to be generated according to an input operation from the input interface 17a.

The communication control interface 17q controls communication with other devices via the network 50. For example, the communication control interface 17g transfers a mammographic image generated by the image processing circuitry 17d to another device via the network 50. The mammographic image transferred via the network 50 can be displayed on the device to which the mammographic image is transferred or undergo image processing in the device to which the mammographic image is transferred.

The system control circuitry 17h is connected to the input interface 17a, the lifting-up/down drive circuitry 17b, the high-voltage generator 17c, the X-ray diaphragm 15b, the image processing circuitry 17d and the communication control interface 17g, and the system control circuitry 17h generally controls the entire mammography device 10.

FIG. 1 will be referred back here. The ultrasound diagnostic device 20 generates an ultrasound image on the basis of reflected-wave data that is collected by scanning the subject with an ultrasound probe that transmits and receives ultrasound.

Figure 4:
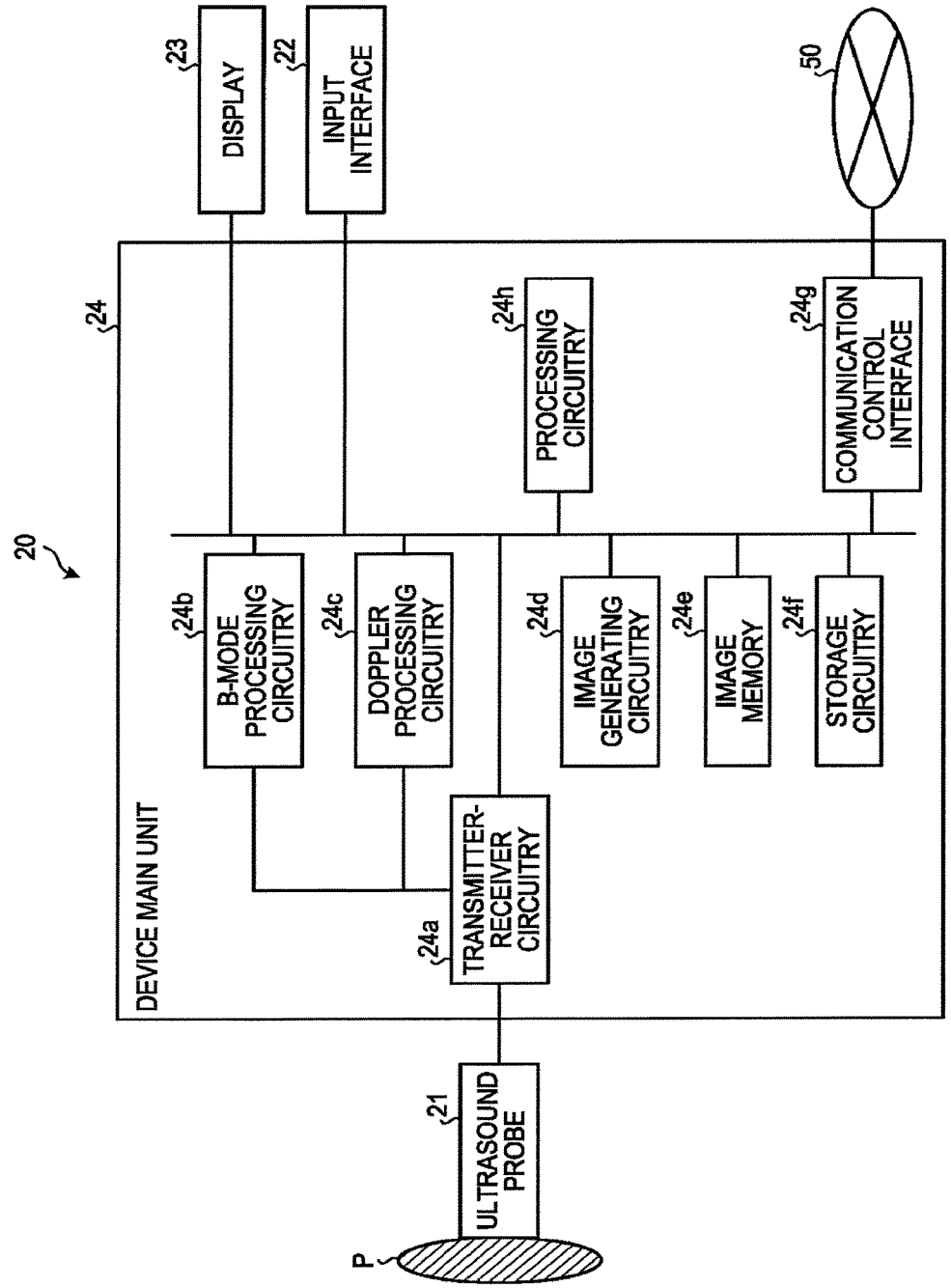
FIG. 4 is a diagram illustrating an exemplary configuration of an ultrasound diagnostic device according to the first embodiment.

FIG. 4 is a diagram illustrating an exemplary configuration of the ultrasound diagnostic device 20 according to the first embodiment. As illustrated in FIG. 4, the ultrasound diagnostic device 20 according to the first embodiment includes an ultrasound probe 21, an input interface 22, a display 23 and a device main unit 24. The ultrasound probe 21 is communicably connected to transmitter-receiver circuitry 24a of the device main unit 24, which will be described below 24. The input interface 22 and the display 23 are communicably connected to various circuitry of the device main unit 24.

The ultrasound probe 21 makes contact with the body surface of a subject P and transmits and receives ultrasound. For example, the ultrasound probe 21 includes multiple piezoelectric vibrators (also referred to as vibratos). The multiple piezoelectric vibrators generate ultrasound according to a transmission signal that is supplied from the transmitter-receiver circuitry 24a. The generated ultrasound is reflected the body tissue of the subject P and then received by the multiple piezoelectric vibrators as reflected-wave signals. The ultrasound probe 21 transmits the reflected-wave signals to the transmitter-receiver circuitry 24a.

For the ultrasound probe 21 according to the first embodiment, a 1D array probe that scans a two-dimensional area (two-dimensional scanning) in the subject P, or a 4D or a 2D array probe that scans a three-dimensional area (three-dimensional scanning) in the subject P may be used.

The input interface 22 corresponds to, for example, a mouse, a keyboard, a button, a panel switch, a touch command screen, a foot switch, a trackball and a joystick. The input interface 22 receives various setting requests from the operator of the ultrasound diagnostic device 20 and properly transfers the received various setting requests to each circuitry of the device main unit 24.

The display 23 displays a graphical user interface (GUI) for the operator to input various setting requests with the input interface 22 and displays images based on the ultrasound image data generated by the device main unit 24 (ultrasound images).

The device main unit 24 is a device that generates ultrasound image data on the basis of the reflected wave signals received by the ultrasound probe 21. As illustrated in FIG. 4, the device main unit 24 includes, for example, the transmitter-receiver circuitry 24a, B-mode processing circuitry 24b, Doppler processing circuitry 24c, image generating circuitry 24d, an image memory 24e, storage circuitry 24f, a communication control interface 24g, and processing circuitry 24h. The transmitter-receiver circuitry 24a, the B-mode processing circuitry 24b, the Doppler processing circuitry 24c, the image generating circuitry 24d, the image memory 24e, the storage circuitry 24f, the communication control interface 24g, and the processing circuitry 24h are communicably connected with one another.

The transmitter-receiver circuitry 24a controls transmission and reception of ultrasound performed by the ultrasound probe 21. For example, the transmitter-receiver circuitry 24a controls transmission and reception of ultrasound performed by the ultrasound probe 21 according to an instruction from the processing circuitry 24h to be described below. The transmitter-receiver circuitry 24a generates transmission waveform data and generates, from the transmission waveform data, a transmission signal for the ultrasound probe 21 to transmit ultrasound. The transmitter-receiver circuitry 24a applies the transmission signal to the ultrasound probe 21 to cause the ultrasound probe 21 to transmit an ultrasound beam that is a flux of ultrasound in the form of beam.

The transmitter-receiver circuitry 24a generates reflected-wave data in which reflected components are enhanced from the direction corresponding to the reception directionality of the reflected wave signal by performing an adding operation by applying a given delay to the reflected wave signal received by the ultrasound probe 21 and transmits the generated reflected-wave data to the B-mode processing circuitry 24b and the Doppler processing circuitry 24c.

For example, the transmitter-receiver circuitry 24a includes an amplifier circuit (referred to as "Amp" as appropriate), an analog/digital (A/D) converter (referred to as "ADC" as appropriate), a generation circuit and a quadrature detection circuit (referred to as "IQ" as appropriate). The amplifier circuit performs gain correction processing by amplifying the reflected wave signal for each channel. The A/D converter performs A/D conversion on the reflected wave signal on which gain correction has been performed.

The generation circuit applies a reception delay necessary to determine reception directionality to the digital data. The generation circuit then performs an operation of adding the reflected-wave signal to which the reception delay is applied. The adding operation performed by the generation circuit enhances the reflected components from the direction corresponding to the reception directionality of the reflected-wave signal.

The quadrature detection circuit converts the output signal of the adder into an in-phase (I) signal and a quadrature-phase (Q) signal of the baseband. The quadrature detection circuit stores the I signal and the Q signal (referred to as the IQ signal below) as the reflected-wave data in the buffer. The quadrature detection circuit may store the output signal of the adder in the buffer after converting the output signal into a radio frequency (RF) signal. The IQ signal and the RE signal are signals containing the phase information (reception signal). The quadrature detection circuit has been described as one that is arranged in a latter stage with respect to the generation circuit; however, the embodiments are not limited thereto. For example, the quadrature detection circuit may be arranged in a former stage with respect to the generation circuit. In that case, the generation circuit performs an operation of summing the I signal and the Q signal.

The B-mode processing circuitry 24b performs various types of signal processing on the reflected-wave data that is generated by the transmitter-receiver circuitry 24a from the reflected-wave signals. The B-mode processing circuitry 24b performs logarithmic amplification, envelope detection, etc., on the reflected-wave data, which is received from the transmitter-receiver circuitry 24a, to generate data (B-mode data) in which the signal intensity at each sample point (observation point) is expressed in luminance. The B-mode processing circuitry 24b transmits the generated B-mode data to the image generating circuitry 24d.

From the reflected wave data received from the transmitter-receiver circuitry 24a, the Doppler processing circuitry 24c generates data (Doppler data) obtained by extracting kinetic information based on the Doppler effect of a mobile object at each sample point within a scanning area. Specifically, the Doppler processing circuitry 24c generates Doppler data obtained by extracting an average speed, a variance, a power value, etc., at each sample point as tue kinetic information about the mobile object. The mobile object is, for example, a blood flow, tissue, such as a wall of the heart, or a contrast agent. The Doppler processing circuitry 24c transmits the generated Doppler data to the image generating circuitry 24d.

The image generating circuitry 24d generates ultrasound image data from the data generated by the B-mode processing circuitry 24b and the Doppler processing circuitry 24c. For example, from the B-mode data that is generated by the B-mode processing circuitry 24b, the image generating circuitry 24d generates B-mode image data representing the intensity of the reflected waves by luminance. From the Doppler data generated by the Doppler processing circuitry 24c, the image generating circuitry 24d then generates Doppler image data representing mobile object information. The Doppler image data is speed image data, dispersion image data, power image data or a combination thereof.

The image memory 24e is a memory that stores the data that is generated by the B-mode processing circuitry 24b, the Doppler processing circuitry 24c, and the image generating circuitry 24d. For example, after diagnosis, it is possible for the operator all up images recorded during the examination and to reproduce an image as a still image or use multiple images to reproduce the images as a video image. The image memory 24e may store the image luminance signal having passing through the transmitter-receiver circuitry 24a, other sets of raw data, and image data that is acquired via the network 50.

The storage circuitry 24f stores a device control program for performing transmission and reception of ultrasound, image processing and display processing and various types of data, such as diagnostic information (such as a patient ID and doctor's findings), diagnosis protocols and various types of setting information. The storage circuitry 24f may be used to keep images stored in the image memory 24e. Furthermore, it is possible to transfer the data stored in the storage circuitry 24f to external devices via an interface (not illustrated in the drawing).

Figure 5:
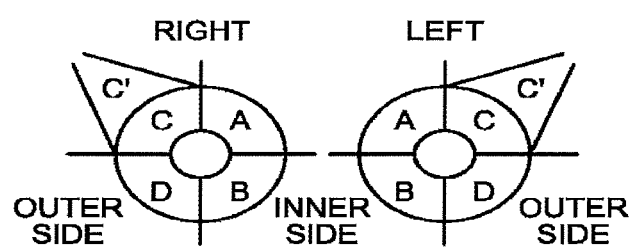
FIG. 5 is a diagram illustrating an exemplary body mark according to the first embodiment.

The storage circuitry 24f stores a body mark. FIG. 5 is a diagram illustrating an exemplary body mark according to the first embodiment. The example illustrated in FIG. 5 represents a schematic diagram of a mammary gland area as an exemplary body mark schematically representing breasts. For example, as illustrated in FIG. 5, the schematic diagram of the mammary gland area includes circular areas respectively indicating the areas of the left and right breasts (hereinafter, breast areas) and approximately triangular areas each indicating the area of an axilla (hereinafter, axilla area).

Each of the circular areas indicating the breast areas is divided vertically and horizontally into four areas "A" to "D". For example, the area "A" (hereinafter, A area) indicates an inner upper area of the breast and the area "B" (hereinafter, B area) indicates an inner lower area of the breast. The area "C" (hereinafter, C area) indicates an outer upper area of the breast and the area "D" (hereinafter, D area) indicates an outer lower area of the breast. The approximately triangular area "C'" (hereinafter, C' area) indicating the axilla area extends from the area C obliquely upward and has a shape narrowing as it is distant from the area C. Furthermore, for example, an area "E" (hereinafter, E area) not illustrated in FIG. 5 indicates the part of an areola. Various diagrams may be used as the schematic diagram as long as the diagrams represent a positional relation about the breast.

The communication control interface 24g controls communication that is made with other devices via the network 50. For example, the communication control interface 24g transfers an ultrasound image generated by the image generating circuitry 24d to another device via the network 50. The ultrasound image transferred via the network 50 can be displayed on the device to which the ultrasound image is transferred or undergo image processing in the device to which the mammographic image is transferred.

The processing circuitry 24h controls the entire process performed by the ultrasound diagnostic device 20. Specifically, the processing circuitry 24h controls the processes performed by the transmitter-receiver circuitry 24a, the B-mode processing circuitry 24b, the Doppler processing circuitry 24c, and the image generating circuitry 24d according to various setting requests that are input by the operator via the input interface 22 and the various control programs and various types of data that are read from the storage circuitry 24f. The processing circuitry 24h causes the display 23 to display the ultrasound image data stored in the image memory 24e.

FIG. 1 will be referred back here. The image processing device 30 processes the mammographic images generated by the mammography device 10 and the ultrasound images generated by the ultrasound diagnostic device 20. The image processing device 30 is mainly used when mammography examination is performed by a mammography examination technologist. The image processing device 30 receives an input of findings on the mammographic images from the mammography examination technologist and stores information representing the received findings as findings information. For example, the image processing device 30 is an image storage server or a work station.

The image display device 40 acquires, for example, a mammographic image, an ultrasound image and findings information about the mammographic image from the image processing device 30 and displays the images and information. The image display device 40 is mainly used when an ultrasound examination technologist performs ultrasound examination. For example, the image display device 40 is a tablet terminal that is portable by the operator and that is connectable to the network 50 via a wireless local area network (LAN). The image display device 40 may be, for example, a laptop personal computer or a desktop personal computer.

Figure 6:
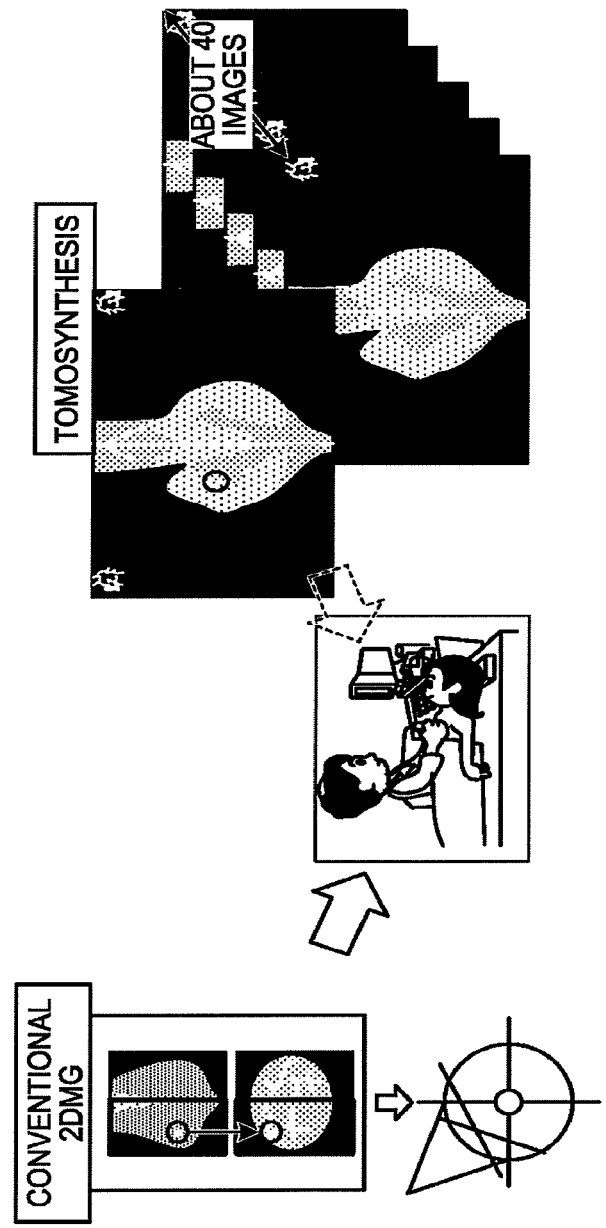
FIG. 6 is a diagram illustrating an exemplary breast image diagnosis using both Tomosynthesis images and ultrasound images.

In breast cancer screening, the medical information processing system 100 described above makes a breast imaging diagnosis using both Tomosynthesis images and ultrasound images. FIG. 6 is a diagram illustrating an exemplary breast imaging diagnosis using both Tomosynthesis images and ultrasound images.

Conventionally, when ultrasound examination is carried out with reference to two-dimensional mammographic images (2DMG), an ultrasound examination technologist understands the two-dimensional mammographic images and comprehends the correspondence relation between a region of interest that is set in the two-dimensional mammographic images and a position of imaging performed by an ultrasound diagnostic device (see the upper left view in FIG. 6). The region of interest is, for example, a site that is determined as a site highly likely to be a site of lesion in the mammographic image, and a site assumed to require careful examination by ultrasound scanning is set as the region of interest. Similarly, when performing ultrasound examination with reference to Tomosynthesis images, the ultrasound examiner has to comprehend the correspondence relation between a region of interest in the Tomosynthesis images and a position of imaging performed by the ultrasound diagnostic device (see the right view in FIG. 6).

The two-dimensional mammographic images or the Tomosynthesis images are captured while the breast is kept pressed. During ultrasound examination, the subject lies with his/her face up. In other words, the condition of the breast is different between the two-dimensional mammographic images or the Tomosynthesis images and ultrasound images. For this reason, it is not easy to comprehend the correspondence relation between the region of interest in the two-dimensional mammographic images or the Tomosynthesis images and the region of interest in the ultrasound images.

A technology of representing a correspondence relation with a position of imaging performed by the ultrasound diagnostic device on a schematic view of a breast generated by the ultrasound diagnostic device by using a two-dimensional mammographic MLO image and a two-dimensional mammographic CC image has been disclosed (see lower left view in FIG. 6). This technology however does not represent the correspondence relation with the position of imaging performed by the ultrasound diagnostic device by using a MLO Tomosynthesis image and a CC Tomosynthesis image.

Furthermore, in a Tomosynthesis image, due to the reconstruction algorithm, when an extremely small subject, such as microcalcification, does not exist on a reconstructed cross section, a blur may occur in the subject or the subject is not necessarily imaged. In order to give better diagnosis by using Tomosynthesis images, it is important to avoid overlap between areas of interest and overlap between a region of interest and mammary gland tissue and set a region of interest in a proper cross section.

For this reason, in diagnosis using breast images between which the shape of the subject differs, the image processing device 30 according to the first embodiment associates the region of interest in MLO Tomosynthesis images or CC MLO Tomosynthesis images with the position of imaging performed by the ultrasound diagnostic device. Details of the image processing device 30 will be described below.

Figure 7:
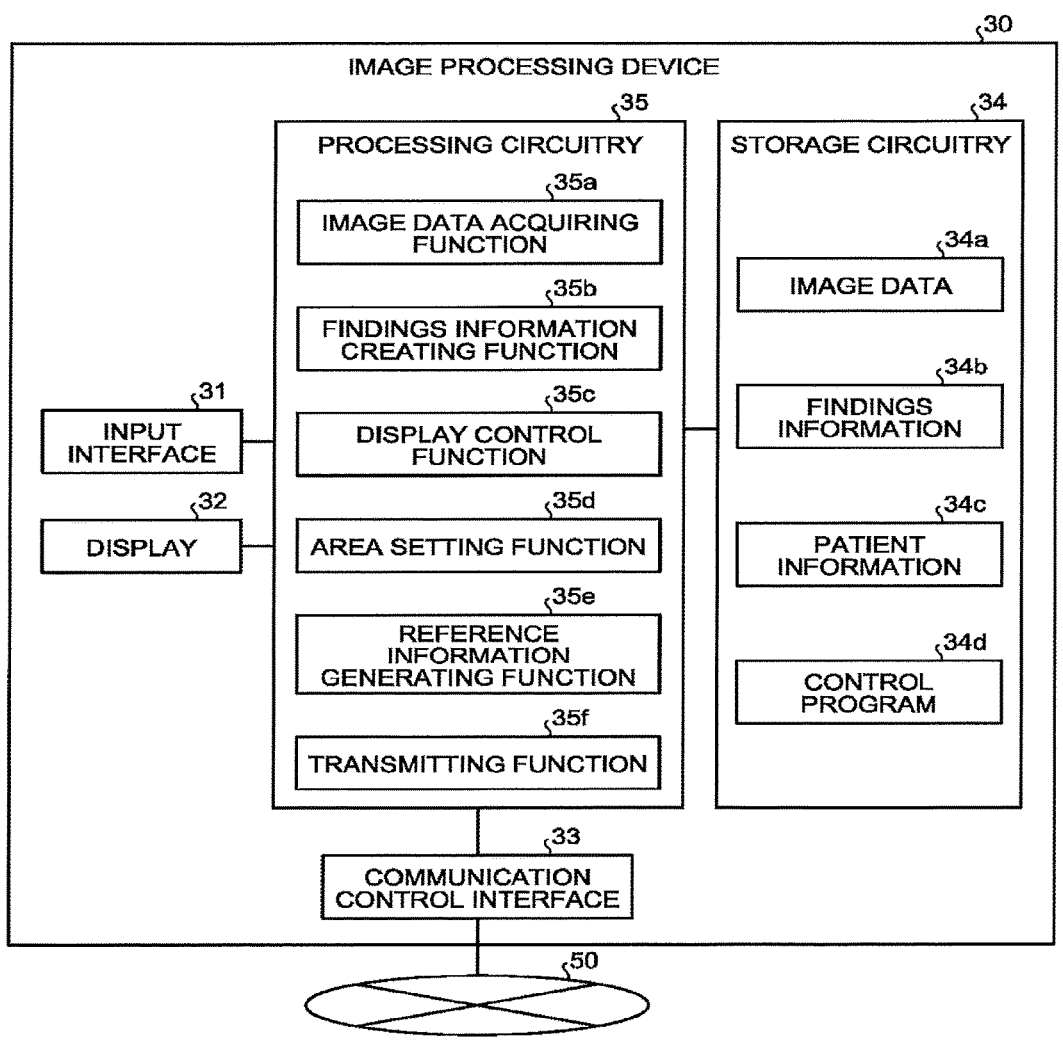
FIG. 7 is a diagram illustrating an exemplary configuration of an image processing device according to the first embodiment.

FIG. 7 is a diagram illustrating an exemplary configuration of the image processing device 30 according to the first embodiment. As illustrated in FIG. 7, the image processing device 30 includes an input interface 31, a display 32, a communication control interface 33, storage circuitry 34, and processing circuitry 35.

The input interface 31 receives inputs of various operations and various types of information from the operator. For example, the input interface 31 includes a keyboard, mouse, a button, a trackball, and a touch panel.

The display 32 displays a GUI for receiving various operations from the operator and various images. For example, the display 32 is a liquid crystal display, a cathode ray tube (CRT) display, or a touch panel.

The communication control interface 33 controls communication made with other devices via the network 50. For example, the communication control interface 33 is a network card or a network adapter that it connected to the network 50 via Ethernet (trademark) or a LAN to communicate with another device. Furthermore, for example, the communication control interface 33 is connected to the network 50 via a wireless LAN to perform wireless communication with another device.

The storage circuitry 34 is a storage device that stores various types of data, such as image data 34a, findings information 34b and the patient information, and a control program 34d for performing image processing and display processing. The data stored in the storage circuitry 34 is transferrable to external devices via an interface (not illustrated in the drawing).

The various types of data stored in the storage circuitry 34 will be described. For example, the storage circuitry 34 stores, as the image data 34a, mammographic images obtained by imaging a breast of a subject and information representing the directions in which the mammographic images are captured. Specifically, the storage circuitry 34 stores each mammographic image and information representing an imaging direction in association with each other. An image data acquiring function 35a to be described below stores mammographic images and sets of information each of which represents an imaging direction in the storage circuitry 34.

More specifically, the storage circuitry stores an MLO image and a CC image. The storage circuitry further stores an MLO Tomosynthesis image and a CC Tomosynthesis image. Information representing the imaging direction is, for example, positional information represented by a device coordinate system of the mammography device. The positional information is added to each image as additional information when the mammography device generates a mammographic image.

Furthermore, for example, the storage circuitry 34 stores the findings information 34b about the mammographic image of the subject. A findings information creating function 35b to be described below stores the findings information in the storage circuitry 34.

Furthermore, for example, the storage circuitry 34 stores patient information 34c enabling uniquely identifying patients. For example, the patient information 34c contains the patent identifier (ID), name, age, and history of diagnosis. For example, the storage circuitry 34 further stores the control program 34d. The control program 34d contains programs corresponding to the respective functions. The control program 34d is read by the processing circuitry 35. The processing circuitry 35 implements the functions corresponding to the respective programs by executing the control program 34d that is read from the storage circuitry 34.

The processing circuitry 35 controls operations of the image processing device 30. As illustrated in FIG. 7, the processing circuitry 35 implements the image data acquiring function 35a, the findings information creating function 35b, a display control function 35c, an area setting function 35d, a reference information generating function 35e, and a transmitting function 35f. For example, the processing functions implemented by the image data acquiring function 35a, the findings information creating function 35b, the display control function 35c, the area setting function 35d, the reference information generating function 35e, and the transmitting function 35f are recorded in the storage circuitry 34 in a form of computer-executable program. The processing circuitry 35 is a processor that reads each program from the storage circuitry 34 and executes the program to implement the function corresponding to the program. In other words, the processing circuitry 35 having read each program has each corresponding function illustrated in the processing circuitry 35 in FIG. 7.

The image data acquiring function 35a acquires a mammographic image obtained by imaging the breast of the subject and information indicating the direction in which the mammographic image is captured. Specifically, the image data acquiring function 35a acquires the mammographic image about the subject to be diagnosed and the information representing the direction in which the mammographic image is captured by communicating with the mammography device 10 via the communication control interface 33 and stores the acquired mammographic image and the information indicating the imaging direction in the storage circuitry 34. The image data acquiring function 35a acquires at least any one of an SILO Tomosynthesis image and a CC Tomosynthesis image of any one of the left and right breasts of the subject.

The findings information creating function 35b creates findings information about the mammographic image of the subject on the basis of the interpretation that is input by the operator. Specifically, the findings information creating function 35*b* receives an input of findings on the mammographic image from the mammography examination technologist via the input interface 31. The findings information creating function 35*b* then creates findings information representing the received findings. The findings information creating function 35*b* stores the created findings information in the storage circuitry 34.

The display control function 35*c* displays a reference image for referring to the mammographic image on the display 32. Specifically, when the display control function 35*c* receives a display request from the operator via the input interface 31, the display control function 35*c* reads the mammographic image about the subject to be diagnosed from the storage circuitry 34 and reads the findings information 34*b* about the subject to be diagnosed from the storage circuitry 34. The display control function 35*0* then displays the reference screen on which the read mammographic image and findings information 34*b* are arranged on the display 32.

The area setting function 35*d* sets a region of interest in a three-dimensional image that is generated by emitting X-rays from the X-ray tube 15*a* to the breast of the subject and imaging the breast from different directions. Specifically, the area setting function 35*d* receives, from the operator, an operation of specifying an area in a given size in a given position on the Tomosynthesis image that is arranged on the reference screen displayed by the display control function 35*c*. The area setting function 35*d* sets a region of interest on a cross section selected by the operator. For example, the operator sets a region of interest on a cross section on which the region of interest is most observable. The area setting function 35*d* sets the area specified by the operator as a region of interest.

For example, the area setting function 35*d* may automatically detect a possible area of site of lesion from the mammographic image by using a CAD (Computer-Aided Diagnosis) function and set the detected area as a region of interest. In other words, the area setting function 35*d* sets a region of interest on the basis of the result of the CAD function. Furthermore, with respect to an area that is detected by the CAD function, the area setting function 35*d* may receive an operation of selecting an area from an area detected by the CAD function and set the selected area as a region of interest. The area setting function 35*d* is examples of setting circuitry.

The reference information generating function 35*e* generates reference information in which the positional information about the region of interest is associated with the schematic diagram of the breast. For example, the reference information generating function 35*e* generates reference information in which positional information representing a relative position of the region of interest on the three-dimensional image is associated with the schematic diagram of the breast. The reference information generating function 35*e* specifies a cross section containing the region of interest in the three-dimensional image and uses, as positional information, the relative position on the cross section in the three-dimensional image and the relative position of the region of interest on the cross section.

Figure 11:
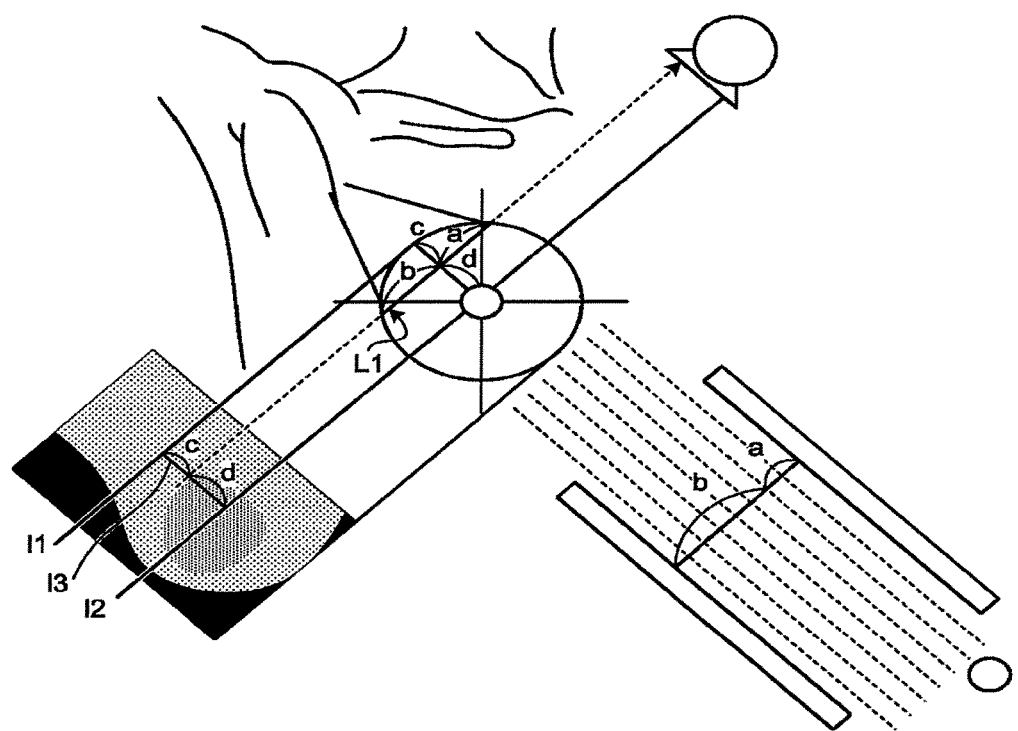
FIG. 11 is a diagram (4) for describing the first embodiment.

With reference to FIGS. 8 to 11, the process operations performed by the reference information generating function 35*e* will be described. FIG. 8 is a flowchart illustrating a process procedure performed by the image processing device 30 according to the first embodiment. FIGS. 9A to 9C are diagrams for describing the first embodiment. FIG. 10 is a flowchart illustrating a process procedure performed by the image processing device 30 according to the first embodiment and FIG. 11 is a diagram for describing the first embodiment. FIG. 8 and FIGS. 9A to 9C illustrate the case where a CC Tomosynthesis image is used and FIG. 10 and FIG. 11 illustrate a case where a MLO Tomosynthesis image is used First of all, the case where a CC Tomosynthesis image is used will be described. As illustrated in FIG. 8, the reference information generating function 35*e* calculates a ratio (a:b) based on an intersection between a cross section containing a region of interest in a Tomosynthesis image and a straight line connecting the press board 14 and the X-ray detector 16*a* in the shortest distance (step S101). FIG. 9A illustrates the case where the breast of the subject is pressed and fixed between the press board 14 and the X-ray detector 16*a*. Each cross section of the Tomosynthesis image, which is generated when Tomosynthesis imaging is performed while the breast is being in the above-described state, is indicated by a dotted line. The example illustrated in FIG. 9A illustrates that the region of interest is contained in the second cross section from the press board 14. As illustrated in FIG. 9A, the reference information generating function 35*e* calculates a ratio (a:b) based on the intersection between the straight line connecting the press board 14 and the X-ray detector 16*a* in the shortest distance and the cross section containing the region of interest in the Tomosynthesis image. In other words, the reference information generating function 35*e* indicates the relative position of the region of interest by using the ratio of the distance from the press board 14 to the region of interest and the distance from the X-ray detector 16*a* to the region of interest.

Figure 9A:
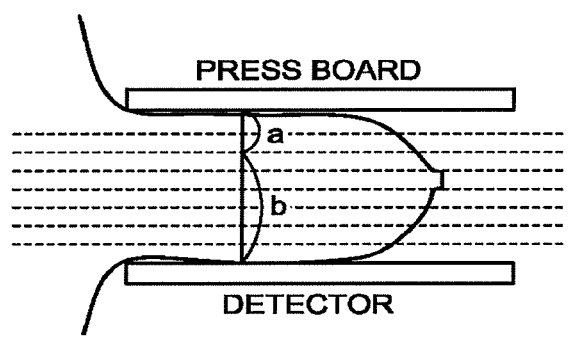
FIG. 9A is a diagram (1) for describing the first embodiment.
Figure 9B:
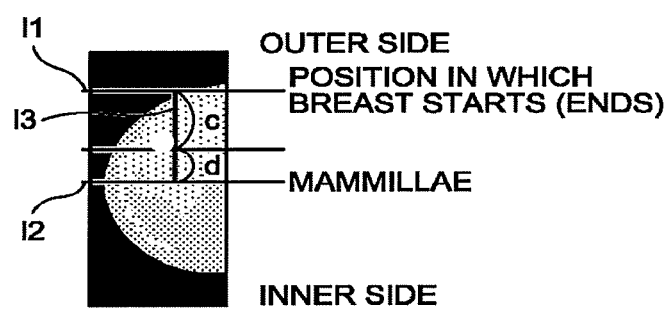
FIG. 9B is a diagram (2) for describing the first embodiment.

The reference information generating function 35*e* detects the boundary of the Tomosynthesis image containing the region of interest and the mammilla (step S102). FIG. 9B illustrates a CC Tomosynthesis image of the right breast. As illustrated in FIG. 9B, the reference information generating function 35*e* detects a position in which the breast starts (ends) and the mammilla as the boundary of the Tomosynthesis image. As illustrated in FIG. 9B, the reference information generating function 35*e* makes a setting such that a straight line 13 connecting a straight line 11 passing through the detected position in which the breast starts (ends) and parallel to an X-axis and a straight line 12 passing through the mammilla in the shortest distance passes through the region of interest and the reference information generating function 35*e* calculates a ratio (c:d) based on the position of the region of interest (step S103). In FIG. 9B, the region of interest is indicated with a circle. In other words, the reference information generating function 35*e* indicates the relative position of the region of interest by using the ratio of the distance from the mammilla to the region of interest and the distance from the position in which the breast starts or the position in which the breast ends to the region of interest.

Figure 9C:
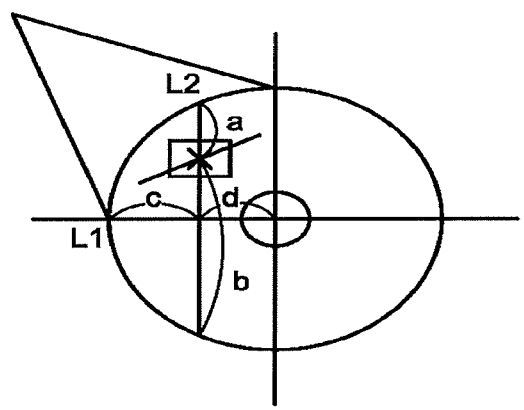
FIG. 9C is a diagram (3) for describing the first embodiment.

As illustrated in FIG. 9C, the reference information generating function 35*e* sets a straight line L2 that passes through a point forming the ratio c:d on a straight line L1 passing through the mammilla and perpendicular to the body axis and that is parallel to the body axis (step S104). The reference information generating function 35*e* then determines a point forming the ratio a:b on the straight line L2 S105). FIG. 9C represents a schematic view of the right breast. In FIG. 9C, the region of interest is indicated with the x sign and an area containing the region of interest is indicated with a rectangle. Furthermore, in FIG. 9C, a probe sign indicating the ultrasound probe 21 is represented in the position where contact of the ultrasound probe 21 is recommended.

The case where an MLO Tomosynthesis image is used will be described. As illustrated in FIG. 10, the reference information generating function 35e calculates a ratio (a:b) based on an intersection between a cross section containing a region of interest in a Tomosynthesis image and a straight line connecting the press board 14 and the X-ray detector 16a in the shortest distance (step S201). FIG. 11 illustrates the case where the breast of the subject is pressed and fixed between the press board 14 and the X-ray detector 16a. Each cross section of the Tomosynthesis image, which is generated when Tomosynthesis imaging is performed while the breast is being in the above-described state, is indicated by a dotted line. The example illustrated in FIG. 11 illustrates that the region of interest is contained in the second cross section from the press board 14. As illustrated in FIG. 11, the reference information generating function 35e calculates a ratio (a:b) based on the intersection between the straight line connecting the press board 14 and the X-ray detector 16a in the shortest distance and the cross section containing the region of interest in the Tomosynthesis image. In other words, the reference information generating function 35e indicates the relative position of the region of interest by using the ratio of the distance from the press board 14 to the region of interest and the distance from the X-ray detector 16a to the region of interest.

The reference information generating function 35e detects the boundary of the Tomosynthesis image containing the region of interest and the mammilla (step S222). FIG. 11 illustrates a MLO Tomosynthesis image of the right breast. As illustrated in FIG. 11, the reference information generating function 35e detects a position in which the breast starts (ends) and the mammilla as the boundary of the Tomosynthesis image. As illustrated in FIG. 11, the reference information generating function 35e makes a setting such that a straight line 13 connecting a straight line 11 passing through the detected position in which the breast starts (ends) and projected to the side of the X-ray tube 15a and a straight line 12 passing through the mammilla in the shortest distance passes through the region of interest and the reference information generating function 35e calculates a ratio (c:d) based on the position of the region of interest (step S203). In other words, the reference information generating function 35e indicates the relative position of the region of interest by using the ratio of the distance from the mammilla to the region of interest and the distance from the position in which the breast starts or the position in which the breast ends to the region of interest.

As illustrated in FIG. 11, the reference information generating function 35e generates a straight line L1 connecting the intersections on the schematic diagram by projecting the region of interest to the side of the X-ray tube 15a (step S204). For example, the reference information generating function 35e projects the region of interest to the side of the X-ray tube 15a, specifies intersections between the projected region of interest and the schematic diagram, and generates the straight line Li connecting the intersections on the schematic diagram. The reference information generating function 35e then calculates a point forming the ratio a:b on the straight line L1 (step S205). FIG. 11 illustrates a schematic diagram of the right breast.

The reference information generating function 35e generates reference information as image data in, for example, the DICOM format or a format, such as, JPEG (Joint Photographic Experts Group), the Graphics interchange Format (GIF) or bitmap. The reference information generating function 35e generates reference information with which identifying information enabling uniquely identifying the subject (patient ID) is further associated and stores the reference information in the storage circuitry 34.

Figure 12:
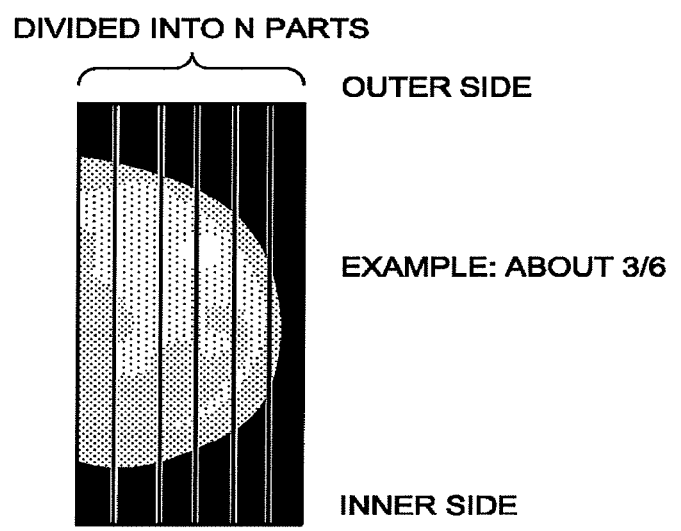
FIG. 12 is a diagram (5) for describing the first embodiment.

The reference information generating function 35e may further generate depth information representing the position in which the region of interest is by using the position in the depth direction with respect to the direction of the body axis from the mammilla. FIG. 12 is a diagram for describing the first embodiment. FIG. 12 illustrates a CC Tomosynthesis image of the right breast. FIG. 12 illustrates an exemplary case where the region of interest is indicated with a circle and the breast is divided into six parts along the direction of the chest wall from the mammilla. As illustrated in FIG. 12, the reference information generating function generates depth information depicting five straight lines on the CC Tomosynthesis image such that the breast is divided into six parts. In such a case, the reference information generating function 35e may indicate a relative position of the region of interest in the position in the depth direction with respect to the chest wall direction from the side of the mammilla. For example, when the region of interest is in the third area from the side of the mammilla in the breast divided into six parts, the reference information generating function 35e may generate "abut 3/6" as depth information. FIG. 12 illustrates the case where the breast is divided into six parts; however, it is possible to set any number for the number of parts into which the breast is divided. The reference information generating function 35e further associates the identifying information enabling uniquely identifying the subject with the generated depth information and then stores the information in the storage circuitry 34. The reference information generating function 35e is examples of generating circuitry.

FIG. 7 will be referred back here. The transmitting function 35f transmits the reference information, which is generated by the reference information generating function 35e, to at least any one of the ultrasound diagnostic device 20 and the image display device 40 according to an instruction from the operator. Specifically, the transmitting function 35f receives, via the input interface 31, an instruction to transmit the reference information from the operator of the image processing device 30 or the ultrasound diagnostic device 20. The transmitting function 35f specifies identifying information enabling uniquely identifying the subject and receives an instruction to transmit the reference information. On receiving the instruction to transmit the reference information, the transmitting function 35f acquires the reference information corresponding to the identifying information, which is specified by the operator, and transmits the reference information to at least any one of the ultrasound diagnostic device 20 and the image display device 40. In other words, the transmitting function 35f causes the display that is referred to in ultrasound scanning to display the reference information. The transmitting function 35f is examples f output control circuitry and the display is examples of output circuitry.

Figure 13:
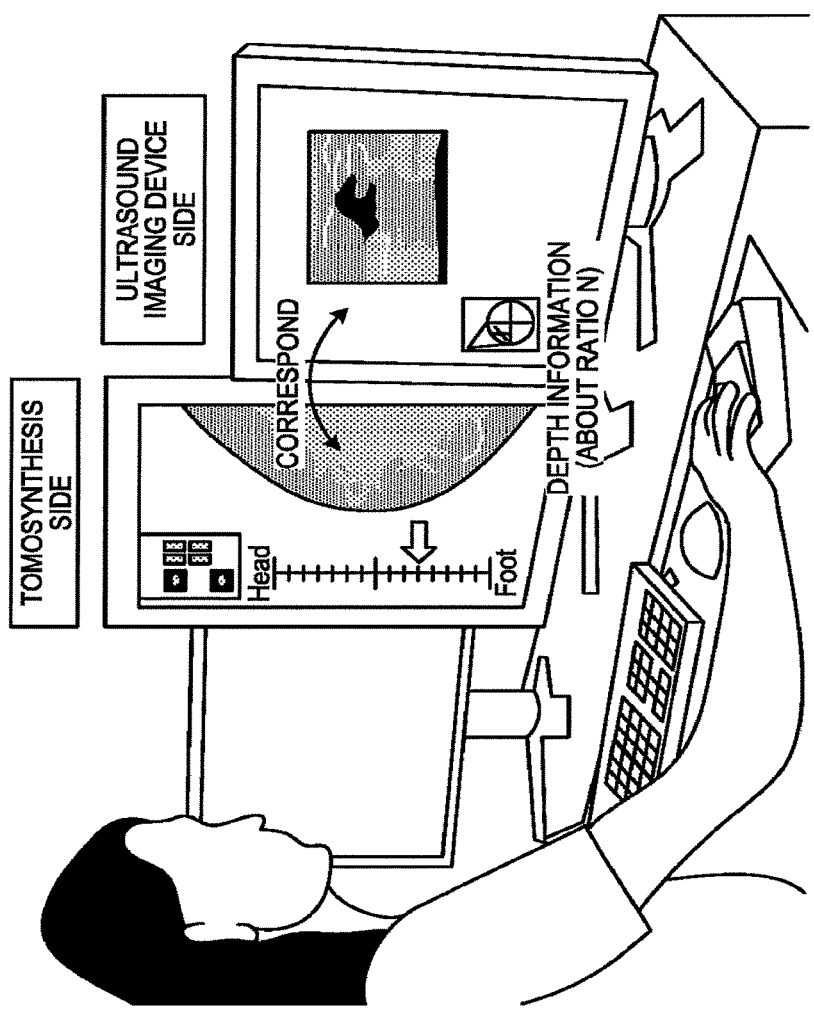
FIG. 13 is a diagram (6) for describing the first embodiment.

FIG. 13 is a diagram for describing the first embodiment. FIG. 13 illustrates the case where the display of the image display device 40 that is referred to in ultrasound scanning is caused to display the reference information. FIG. 13 illustrates the case where the operator of the ultrasound diagnostic device 20 refers to the Tomosynthesis images and the reference information before starting ultrasound scanning and comprehends a site to be scanned in the subject.

As illustrated in FIG. 13, an ultrasound image is displayed on the display of the image display device 40 (on the side of the ultrasound diagnostic device 20 in FIG. 13). The ultrasound image displayed before ultrasound scanning is, for example, an ultrasound image of the same subject that was captured in the past Then, as illustrated in FIG. 13, the reference information is displayed on the lower left side with respect to the ultrasound image. In the example illustrated in FIG. 13, a sign indicating the relative position of a region of interest is displayed on a schematic diagram of the right breast in the reference information. Alternatively, only a sign indicating the relative position of the region of interest may be displayed as the reference information. In addition to the sign indicating the relative position of the region of interest, a ratio representing the relative position in the schematic diagram may be displayed as the reference information. For example, a:b and c:d illustrated in FIG. 9C or a:b and c:d illustrated in the schematic diagram in FIG. 11 may be displayed as the reference information.

The transmitting function 35f further transmits the depth information to the display of the image display device 40. Accordingly, the display of the image display device 40 displays the depth information. For example, the depth information is displayed that represents the number of an area counted from the side of the mammilla in which the region of interest is in the breast that is divided into N parts. For example, when "about 2/5" is displayed as the depth information, the operator of the ultrasound diagnostic device 20 is able to comprehend that the region of interest is in the second area from the side of the mammilla in the breast divided into five parts by referring to the depth information. Accordingly, the operator of the ultrasound diagnostic device 20 is able to comprehend in advance an approximate position of the region of interest on which ultrasound scanning is to be performed in the depth direction.

Furthermore, in the example illustrated in FIG. 13, the display 32 of the image processing device 30 (the Tomosynthesis side in FIG. 13) is arranged adjacently to the display of the image display device 40. In the example illustrated in FIG. 13, a CC Tomosynthesis image is displayed on the display 32 of the image processing device 30. The Tomosynthesis image is a CC Tomosynthesis image that is specified as a cross section containing the region of interest when the reference information displayed on the display of the image display device 40 is generated. In other words, the CC Tomosynthesis image on the display 32 of the image processing device 30 corresponds to the reference information being displayed on the display of the image display device 40.

In the example illustrated in FIG. 13, a scale and an arrow indicating the position of the cross section being displayed on the display 32 of the image processing device 30 are displayed. The upper side of the scale indicates the Head direction and the lower side indicates the Foot direction. The arrow indicates in which position the cross section of the Tomosynthesis image being displayed on the display 32 of the image processing device 30 is when a three dimensional image is sliced in the boy axis direction. The arrow is vertically movable along the scale. When the arrow is moved, a Tomosynthesis image corresponding to the cross section indicated by the moved arrow may be displayed on the display 32 of the image processing device 30.

FIG. 13 illustrates the case where the display of the image display device 40 is caused to display the reference information and the display 32 of the image processing device 30 is caused to display the Tomosynthesis image; however, the embodiments are not limited thereto. For example, when the image display device 40 includes multiple displays, one of the displays may be caused to display the reference information and the other display may be caused to display the Tomosynthesis image.

As described above, in the first embodiment, a region of interest is set in a three-dimensional image that is generated by emitting X-rays from the X-ray tube 15a to a breast of a subject and imaging the breast from different directions. Reference information in which positional information about a region of interest is associated with a schematic diagram of the breast is then generated. A display that is referred to when ultrasound scanning is performed is then caused to output the reference information. Accordingly, the first embodiment enables association between the region of interest in an MLO Tomosynthesis image or a CC Tomosynthesis image and a position of imaging performed by the ultrasound diagnostic device. An ultrasound examiner is able to easily perform ultrasound scanning by using the positional information about the Tomosynthesis image. As a result, it is possible to make the workflow efficient. Associating the position of the region of interest in the Tomosynthesis image and the position of imaging performed by the ultrasound diagnostic device is enabled by using an objective method, which increases reproducibility.

The multiple components in FIG. 7 may be integrated into a single processor to implement the functions of the components. The word "processor" used in the descriptions given above denotes, for example, a central processing unit (CPU), a graphics processing unit (GPU), or a circuit, such as an application specific integrated circuit (ASIC), a programmable logic device (such as a simple programmable logic device (SPLD), a complex programmable logic device (CPLD) or a field programmable gate array (FPGA). The processor implements the functions by reading the program saved in the storage circuitry 34 and executing the program. Instead of being saved in the storage circuitry 34, the program may be directly incorporated in the circuit of the processor. In this case, the functions are implemented by reading the program incorporated in the circuit and reading the program. Each processor of the embodiment is not necessarily configured as a single circuit. Multiple independent circuits may be combined into a single processor to implement the functions.

The first embodiment illustrates the case where the reference information is generated when radiologic interpretation on mammographic images is performed and the generated reference information is displayed on the displayed that is referred to when ultrasound scanning is performed when a request for the reference information is received from the operator of the ultrasound diagnostic device 20; however, the embodiments are not limited thereto. For example, the image processing device 30 may generate reference information on receiving a request to acquire the reference information from the operator of the ultrasound diagnostic device 20. In that case, the image processing device 30 sets a region of interest on a Tomosynthesis image when radiologic interpretation on a mammographic image is performed, associates a patient ID with the Tomosynthesis image and stores the image in the storage circuitry 34. The operator of the ultrasound diagnostic device 20 specifies a patent ID and requests acquisition of the reference information. The image processing device 30 then reads a Tomosynthesis image matching the patient ID and generates reference information.

Other Embodiments

The embodiments are not limited thereto.

The reference information generating function 35e may generate reference information in a mode corresponding to the characteristic of the region of interest. For example, when generating reference information by using a schematic diagram template, the reference information generating function 35e may not only indicate positional information about the region of interest on a schematic diagram but also extract an area having a mammary gland intensity higher than a given value, a calcified area and an area of tumor from the mammographic image and display the areas on the schematic diagram. For example, the reference information generating function 35e may display parts corresponding to these areas in colors different from that of the schematic diagram according to the type of the areas or display signs previously determined according to area types.

Figure 14:
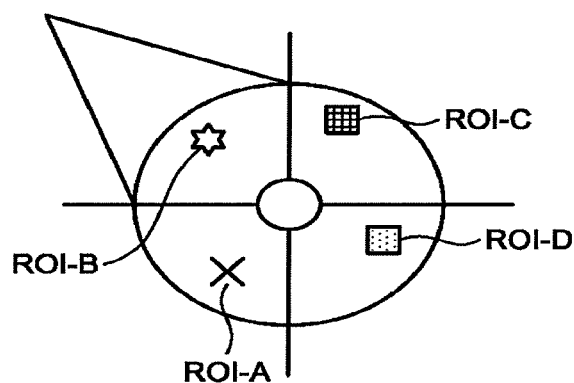
FIG. 14 is a diagram for describing another embodiment.

FIG. 14 is a diagram describing other embodiments. FIG. 14 illustrates a case where ROI-A, ROI-B, ROI-C and ROI-C are set as four regions of interest. ROI-A is denoted by a sign ×. ROI-A is set in a case where a site determined as being less likely to be a site of lesion but determined as requiring ultrasound scanning is a region of interest. ROI-B is denoted by a star sign. ROI-B is set in a case where a site determined as a tumor a region of interest. ROI-C is denoted by a hatched rectangle. ROI-C is set in a case where a site determined as an area having a high density of mammary glands is a region of interest. ROI-D is denoted by a dotted rectangle. ROI-D is set in a case where a site determined as calcified is a region of interest.

The above-described embodiment illustrates that, the image processing device 30 implements the area setting function 35d and the reference information generating function 35e; however, the embodiments are not limited thereto. For example, the image processing device 35 may implement the area setting function 35d and the ultrasound diagnostic device 20 may implement the reference information generating function 35e. Alternatively, the mammography device 10 may implement the area setting function 35d and the ultrasound diagnostic device 20 may implement the reference information generating function 35e. The mammography device 10 may implement the area setting function 35d and the reference information generating function 35e.

The above-described embodiment illustrates the case where the transmitting function 35f causes the display that is referred to by the operator when performing ultrasound scanning to output the reference information; however, the embodiments are not limited thereto. In other words, the timing at which the display is caused to output the reference information is not limited to the time of ultrasound scanning, and the display is caused to output the reference information at given timing.

For example, the above-described embodiment is applicable to the case where radiologic interpretation on an ultrasound image is performed after ultrasound scanning ends. Furthermore, the above-described embodiment is applicable to, for example, the case where the region of interest in the MLO Tomosynthesis image or the CC Tomosynthesis image is checked before ultrasound scanning starts or ultrasound scanning ends. In other words, the transmitting function 35f causes the display that is referred to by the operator to output the reference information before ultrasound scanning starts or after ultrasound scanning ends.

The above-described embodiment illustrates that the transmitting function 35f transmits the reference information to at least any one of the display 23 of the ultrasound diagnostic device 20 and the display of the image display device 40 to cause at least any one of the display 23 and the display of the image display device 40 to serve as examples of output circuitry and output the reference information; however, the embodiments are not limited thereto. For example, the transmitting function 35f may cause the display 17f of the mammography device 10 and the display 32 of the image processing device 30 to serve as examples of output circuitry and output the reference information. Furthermore, for example, when the medical information processing system 100 includes a printer, the transmitting function 35f may cause the printer to serve as examples of output circuitry and output the reference information.

The components of each device illustrated in the drawings in the descriptions of the above-escribed embodiment are functional ideas and thus are not necessarily required to be configured physically as illustrated in the drawings. In other words, specific modes of dispersion and integration among the devices is not limited to those illustrated in the drawings and all or part of the devices may be dispersed or integrated according to given unit functionally or physically according to various loads and the situation in which the devices are used. Furthermore, all or given part of each processing function implemented in each device may be implemented by a CPU and a program that is analyzed and executed by the CPU or may be implemented as hardware using a wired logic.

The control method of the above-described embodiment may be implemented by executing a control program prepared in advance with a computer, such as a personal computer or a work station. The control program may be distributed via a network, such as the Internet. Alternatively, the control program may be recorded in a computer-readable recording medium, such as a hard disk, a flexible disk (FD), a CD-ROM, a MO or a DVD, and may be read by a computer from the recording medium and thus executed.

According to at least one of the above-described embodiments, in screening using both Tomosynthesis images and ultrasound images, it is possible to make a workflow efficient.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system comprising:
    setting circuitry configured to set a region of interest in a three-dimensional image that is generated by emitting X-rays to a breast of a subject and imaging the breast from different directions;
    generating circuitry configured to generate reference information in which positional information about the region of interest is associated with a schematic diagram of the breast; and
    output control circuitry configured to cause output circuitry to output the reference information.

2. The medical information processing system according to claim 1, wherein the generating circuitry is configured to generate the reference information in which the positional information indicating a relative position of the region of interest in the three-dimensional image is associated with the schematic diagram of the breast.

3. The medical information processing system according to claim 2, wherein the generating circuitry is configured to represent the relative position of the region of interest by using a ratio of a distance from press board to the region of interest and a distance from an X-ray detector to the region of interest.

4. The medical information processing system according to claim 2, wherein the generating circuitry is configured to represent the relative position of the region of interest by using a ratio of a distance from a mammilla to the region of interest and a distance from any one of a position in which the breast starts and a position in which the breast ends to the region of interest.

5. The medical information processing system according to claim 2, wherein the generating circuitry is configured to specify a cross section containing the region of interest in the three-dimensional image and configured to use, as the positional information, a relative position of the cross section in the three dimensional image and a relative position of the region of interest in the cross section.

6. The medical information processing system according to claim 1, wherein
the generating circuitry is configured to further generate depth information indicating a position in which the region of interest is by a position in a depth direction with respect to a body axis from the mammilla, and
the output control circuitry is configured to further cause the output circuitry to display the depth information.

7. The medical information processing system according to claim 1, wherein the generating circuitry is configured to generate the reference information in a mode corresponding to a characteristic of the region of interest.

8. The medical information processing system according claim 1, wherein the setting circuitry is configured to set the region of interest on a cross section that is selected by the operator.

9. The medical information processing system according to claim 1, wherein the setting circuitry is configured to set the region of interest according to a result of computer-aided diagnosis.

10. The medical information processing system according to claim 1, further comprising storage circuitry configured to store the reference information,
wherein
the generating circuitry is configured to generate the reference information in which identifying information enabling uniquely identifying the subject is associated and store the reference information in the storage circuitry, and
the output control circuitry is configured to acquire the reference information corresponding to the specified identifying information from the storage circuitry and causes the output circuitry to output the reference information.

11. The medical information processing system according to claim 10, wherein the storage circuitry stores the reference information in the DICOM format or the JPEG format.

12. The medical information processing system according to claim 1, wherein the three-dimensional image is generated on the basis of an image obtained by an X-ray mammography device by Tomosynthesis imaging.

* * * * *